(12) United States Patent
Broering et al.

(10) Patent No.: US 9,486,977 B2
(45) Date of Patent: Nov. 8, 2016

(54) MULTI-PLY PUCKERED FILMS FORMED BY DISCONTINUOUS LAMINATION OF FILMS HAVING DIFFERENT REBOUND RATIOS

(75) Inventors: Shaun T. Broering, Fort Thomas, KY (US); Ken Cisek, Chicago, IL (US); Michael G. Borchardt, Naperville, IL (US)

(73) Assignee: The Glad Products Company, Oakland, CA (US)

( * ) Notice: Subject to any disclaimer, the term of this patent is extended or adjusted under 35 U.S.C. 154(b) by 804 days.

(21) Appl. No.: 13/552,352

(22) Filed: Jul. 18, 2012

(65) Prior Publication Data

US 2014/0023829 A1   Jan. 23, 2014

(51) Int. Cl.
| | |
|---|---|
| B32B 3/26 | (2006.01) |
| B32B 5/14 | (2006.01) |
| B32B 7/04 | (2006.01) |
| B32B 27/08 | (2006.01) |
| B32B 37/14 | (2006.01) |
| A61F 13/51 | (2006.01) |
| B32B 38/00 | (2006.01) |

(52) U.S. Cl.
CPC ............ *B32B 3/263* (2013.01); *A61F 13/51* (2013.01); *B32B 5/142* (2013.01); *B32B 5/147* (2013.01); *B32B 7/045* (2013.01); *B32B 27/08* (2013.01); *B32B 37/144* (2013.01); *B32B 2038/0028* (2013.01); *B32B 2439/00* (2013.01); *B32B 2439/06* (2013.01); *B32B 2555/02* (2013.01); *Y10T 428/24562* (2015.01)

(58) Field of Classification Search
CPC ............. B32B 3/28; B32B 3/30; B32B 3/00; B32B 1/02; B32B 7/045
USPC .......................................... 428/166; 383/109
See application file for complete search history.

(56) References Cited

U.S. PATENT DOCUMENTS

| | | |
|---|---|---|
| 2,714,571 A | 8/1955 | Irion et al. |
| 3,058,868 A | 10/1962 | Schroeder |
| 3,622,422 A | 11/1971 | Newman et al. |
| 3,857,144 A | 12/1974 | Bustin |
| 4,116,892 A | 9/1978 | Schwarz |
| 4,153,664 A | 5/1979 | Sabee |

(Continued)

FOREIGN PATENT DOCUMENTS

KR   10-1032232 B1   5/2011

OTHER PUBLICATIONS

International Search Report, mailed Sep. 4, 2013, from counterpart PCT/US2013/050541, filing date Jul. 15, 2013.

*Primary Examiner* — Aaron Austin
*Assistant Examiner* — Alicia Sawdon
(74) *Attorney, Agent, or Firm* — Thomas C. Feix

(57) ABSTRACT

Methods of increasing the loft of a multi-ply thermoplastic film include stretching thermoplastic films with different rebound ratios, non-continuously laminating the films together, and releasing the films to create puckers in one or more of the films. The puckers can comprise billowing of one of the films. The non-continuous laminated areas can maintain the puckers in the films. The puckers can increase the loft of the film, improve the feel of the film, and/or modify the look of the film. The loft of such multi-ply puckered thermoplastics films vary independent of the basis weight of the films. Thus, multi-ply puckered thermoplastics films with increased loft of one or more implementations can look and feel thicker while using reduced amounts of thermoplastic material.

18 Claims, 9 Drawing Sheets

(56) References Cited

U.S. PATENT DOCUMENTS

| | | | |
|---|---|---|---|
| 4,153,751 A | 5/1979 | Schwarz | |
| 4,289,832 A | 9/1981 | Schwarz | |
| 4,302,495 A | 11/1981 | Marra | |
| 4,343,848 A | 8/1982 | Leonard, Jr. | |
| 4,379,197 A | 4/1983 | Cipriani | |
| 4,438,167 A | 3/1984 | Schwarz | |
| 4,517,714 A | 5/1985 | Sneed et al. | |
| 4,522,203 A | 6/1985 | Mays | |
| 4,614,679 A | 9/1986 | Farrington, Jr. et al. | |
| 4,692,368 A | 9/1987 | Taylor et al. | |
| 4,704,238 A | 11/1987 | Okuyama et al. | |
| 4,753,840 A | 6/1988 | Van Gompel | |
| 4,930,905 A | 6/1990 | Sharps, Jr. | |
| 5,035,941 A | 7/1991 | Blackburn | |
| 5,100,721 A | 3/1992 | Akao | |
| 5,296,184 A | 3/1994 | Wu et al. | |
| 5,382,461 A | 1/1995 | Wu | |
| 5,422,172 A | 6/1995 | Wu | |
| 5,518,801 A | 5/1996 | Chappell et al. | |
| 5,626,944 A * | 5/1997 | Rasmussen | 428/172 |
| H1674 H * | 8/1997 | Ames et al. | 604/389 |
| 5,851,937 A | 12/1998 | Wu et al. | |
| 5,861,074 A | 1/1999 | Wu | |
| 5,865,824 A | 2/1999 | Chen et al. | |
| 5,865,926 A | 2/1999 | Wu et al. | |
| 5,882,769 A * | 3/1999 | McCormack et al. | 428/152 |
| 6,013,151 A | 1/2000 | Wu et al. | |
| 6,214,147 B1 | 4/2001 | Mortellite et al. | |
| 6,254,736 B1 | 7/2001 | Earl et al. | |
| 6,265,045 B1 | 7/2001 | Mushaben | |
| 6,361,784 B1 | 3/2002 | Brennan et al. | |
| 6,385,818 B1 | 5/2002 | Savicki, Sr. | |
| 7,132,151 B2 | 11/2006 | Rasmussen | |
| 7,306,729 B2 | 12/2007 | Bacino et al. | |
| 2002/0074691 A1 | 6/2002 | Mortellite et al. | |
| 2006/0093766 A1 | 5/2006 | Savicki et al. | |
| 2007/0166503 A1 | 7/2007 | Hannigan | |
| 2007/0257402 A1* | 11/2007 | Rasmussen | 264/339 |
| 2008/0124461 A1 | 5/2008 | Leener et al. | |
| 2009/0029114 A1 | 1/2009 | Cancio et al. | |
| 2009/0233041 A1 | 9/2009 | Rasmussen | |
| 2010/0040875 A1* | 2/2010 | Patel et al. | 428/338 |
| 2011/0117307 A1* | 5/2011 | Fraser et al. | 428/66.6 |
| 2012/0064271 A1 | 3/2012 | Broering et al. | |

* cited by examiner

MULTI-PLY PUCKERED FILMS FORMED BY DISCONTINUOUS LAMINATION OF FILMS HAVING DIFFERENT REBOUND RATIOS

BACKGROUND OF THE INVENTION

1. The Field of the Invention

The present invention relates generally to thermoplastic films. Specifically, the invention relates to multi-ply thermoplastic films with increased loft and to methods of manufacturing thermoplastic films to increase the loft thereof.

2. Background and Relevant Art

Thermoplastic films are a common component in various commercial and consumer products. For example, grocery bags, trash bags, sacks, and packaging materials are products that are commonly made from thermoplastic films. Additionally, feminine hygiene products, baby diapers, adult incontinence products, and many other products include thermoplastic films to one extent or another.

The cost to produce products including thermoplastic film is directly related to the cost of the thermoplastic film. Recently the cost of thermoplastic materials has risen. In response, many manufacturers attempt to control manufacturing costs by decreasing the amount of thermoplastic material in a given product. One way manufacturers may attempt to reduce production costs is to use thinner films or stretch the thermoplastic films, thereby increasing surface area and reducing the amount of thermoplastic film needed to produce a product of a given size. These thin films can be manufactured by extruding thinner films or by cold formation stretching films after they are extruded. Unfortunately, stretched or otherwise produced thinner thermoplastic films can have undesirable properties. For example, thinner thermoplastic films can are typically more transparent or translucent and can have reduced physical properties. Additionally, consumers commonly associate thinner looking films with weakness. Such consumers may feel that they are receiving less value for their money when purchasing products with thinner films; and thus, may be dissuaded from purchasing thinner thermoplastic films. Accordingly, there is a need to create thinner films which have good physical properties and have the appearance of thicker, more expensive films.

BRIEF SUMMARY OF THE INVENTION

Implementations of the present invention solve one or more problems in the art with apparatus and methods for creating multi-ply, puckered thermoplastic films. In particular, one or more implementations of the present invention include cold formation stretching one or more film plies and then non-continuously laminating two or more film plies together. Upon releasing the multi-ply thermoplastic film, differences in the rebound ratio of the film plies can cause one or more of the plies to pucker between lamination points thereby increasing the gauge or loft of the film. Additionally, one or more implementations include multi-ply, puckered thermoplastic films with increased loft.

For example, an implementation of a method for forming a multi-ply, puckered thermoplastic film with increased loft can involve providing a first thermoplastic film with a first rebound ratio and providing a second thermoplastic film with a second rebound ratio. The second rebound ratio can differ from the first rebound ratio. The rebound ratios of the first and second thermoplastic films might differ if one has undergone a different type or degree of cold formation stretching or if the first or second thermoplastic films are of different materials or different thicknesses. The method can also involve non-continuously laminating the first and the second thermoplastic films together. The method can then involve releasing one or more of the first and the second thermoplastic films. The first thermoplastic film can rebound more than the second thermoplastic film upon releasing of the films thereby causing puckering of the first thermoplastic film.

Additionally, an implementation of a multi-ply, puckered thermoplastic film formed from first and second thermoplastic films can comprise a first thermoplastic film ply with a first gauge and a second thermoplastic film ply with a second gauge. A plurality of non-continuous laminated areas can bond the first and the second thermoplastic film plies together. The film can also include a plurality of puckers in one or more of the first and the second thermoplastic film plies. The puckers can be located between and maintained by adjacent laminated areas. A loft of the puckers can be greater than a sum of the first gauge and the second gauge.

In addition to the forgoing, a multi-ply, puckered thermoplastic bag can comprise a first ply of thermoplastic material. The first ply can include first and second side walls joined along a bottom edge, a first side edge, and an opposing second side edge. The bag can also include a second ply of thermoplastic material positioned inside the first ply. The second ply can include first and second side walls joined along a bottom edge, a first side edge, and an opposing second side edge. A plurality of non-continuous laminated areas can bond the first ply to the second ply. Additionally, the bag can include a plurality of non-continuous puckers in the first ply.

Additional features and advantages of exemplary embodiments of the present invention will be set forth in the description which follows, and in part will be obvious from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. It should be noted that the figures are not drawn to scale, and that elements of similar structure or function are generally represented by like reference numerals for illustrative purposes throughout the figures. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1A:
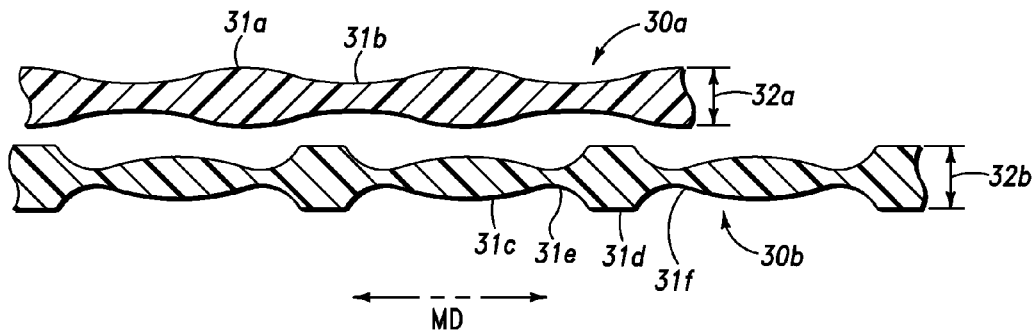
FIG. 1A illustrates a side, cross-sectional view of two thermoplastic films prior to stretching in accordance with one or more implementations of the present invention.

One or more implementations of the present invention include apparatus and methods for creating multi-ply, puckered thermoplastic films. In particular, one or more implementations of the present invention include cold formation stretching one or more film plies and then non-continuously laminating two or more film plies together. Upon releasing the multi-ply thermoplastic film, differences in the rebound ratio of the film plies can cause one or more of the plies to pucker between lamination points thereby increasing the gauge or loft of the film. Additionally, one or more implementations include multi-ply, puckered thermoplastic films with increased loft.

Indeed, one or more implementations of the present invention can provide thermoplastic films, and products made there from, with increased loft created by one or more puckers. The increased loft created by one or more puckers can connote strength to a consumer. Additionally, the puckers can provide the film with increased softness and a desirable look and feel.

Furthermore, implementations of the present invention allow for tailoring (e.g., increasing) of the loft of a film independent of the basis weight (amount of raw material) of the film. Thus, one or more implementations can provide films with increased loft despite a reduction in thermoplastic material. As such, one or more implementations can reduce the material needed to produce a product while maintaining or increasing the loft of the film.

Additionally, consumers may associate thinner films (e.g., films with decreased basis weight) with decreased strength. Indeed, consumers may feel that they are receiving less value for their money when purchasing thermoplastic film products with thinner gauges. One will appreciate in light of the disclosure herein that a consumer may not readily detect that one or more puckered films of the present invention has a reduced basis weight. In particular, by increasing the loft of thinner films, the consumer may perceive the puckered film as being thicker and/or having increased strength.

In addition to the foregoing, one or more implementations provide thermoplastic films with increased loft that consumers can associate with improved properties. For example, the puckered regions can indicate that those regions have undergone a transformation to impart a desirable characteristic to that region (e.g., increased strength or thicker feel). Thus, the puckered regions can serve to notify a consumer that the thermoplastic film has been processed to improve the film.

As explained in greater detail below, the loft of a thermoplastic film can be based, at least in part, on the thermoplastic material of the film being stretched. As an initial matter, the thermoplastic material of the films of one or more implementations can include, but are not limited to, thermoplastic polyolefins, including polyethylene and copolymers thereof and polypropylene and copolymers thereof. The olefin based polymers can include the most common ethylene or propylene based polymers such as polyethylene, polypropylene, and copolymers such as ethylene vinylacetate (EVA), ethylene methyl acrylate (EMA) and ethylene acrylic acid (EAA), or blends of such polyolefins.

Other examples of polymers suitable for use as films in accordance with the present invention include elastomeric polymers. Suitable elastomeric polymers may also be biodegradable or environmentally degradable. Suitable elastomeric polymers for the film include poly(ethylene-butene), poly(ethylene-hexene), poly(ethylene-octene), poly(ethylene-propylene), poly(styrene-butadiene-styrene), poly(styrene-isoprene-styrene), poly(styrene-ethylene-butylene-styrene), poly(ester-ether), poly(ether-amide), poly(ethylene-vinylacetate), poly(ethylene-methylacrylate), poly(ethylene-acrylic acid), poly(ethylene butylacrylate), polyurethane, poly(ethylene-propylene-diene), ethylene-propylene rubber.

In at least one implementation of the present invention, the film can include linear low density polyethylene. The term "linear low density polyethylene" (LLDPE) as used herein is defined to mean a copolymer of ethylene and a minor amount of an alkene containing 4 to 10 carbon atoms, having a density of from about 0.910 to about 0.926, and a melt index (MI) of from about 0.5 to about 10. For example, some implementations of the present invention can use an octene comonomer, solution phase LLDPE (MI=1.1; ρ=0.920). Additionally, other implementations of the present invention can use a gas phase LLDPE, which is a hexene gas phase LLDPE formulated with slip/AB (MI=1.0; ρ=0.920). Still further implementations of the present invention can use a gas phase LLDPE, which is a hexene gas phase LLDPE formulated with slip/AB (MI=1.0; ρ=0.926). One will appreciate that the present invention is not limited to LLDPE, and can include "high density polyethylene" (HDPE), "low density polyethylene" (LDPE), and "very low density polyethylene" (VLDPE). Indeed films made from any of the previously mentioned thermoplastic materials or combinations thereof can be suitable for use with the present invention.

Indeed, implementations of the present invention can include any flexible or pliable thermoplastic material which may be formed or drawn into a web or film. Furthermore, the thermoplastic materials may include a single layer or multiple layers. An example of multilayered films that are suitable for use with one or more implementations of the present invention include coextruded multilayered films. Examples of multi-ply films include multiple films continuously laminated together, and multiple films partially or discontinuously laminated together. The thermoplastic material may be opaque, transparent, translucent, or tinted. Furthermore, the thermoplastic material may be gas permeable or impermeable.

As used herein, the term "flexible" refers to materials that are capable of being flexed or bent, especially repeatedly, such that they are pliant and yieldable in response to externally applied forces. Accordingly, "flexible" is substantially opposite in meaning to the terms inflexible, rigid, or unyielding. Materials and structures that are flexible, therefore, may be altered in shape and structure to accommodate external forces and to conform to the shape of objects brought into contact with them without losing their integrity. In accordance with further prior art materials, web materials are provided which exhibit an "elastic-like" behavior in the direction of applied strain without the use of added traditional elastic. As used herein, the term "elastic-like" describes the behavior of web materials which when subjected to an applied strain, the web materials extend in the direction of applied strain, and when the applied strain is released the web materials return, to a degree, to their pre-strained condition.

In addition to the foregoing, one will appreciate in light of the disclosure herein that manufacturers may form the films or webs to be used with the present invention using a wide variety of techniques. For example, a manufacturer can form the films using conventional flat or cast extrusion or coextrusion to produce monolayer, bilayer, or multilayer films. Alternatively, a manufacturer can form the films using suitable processes, such as, a blown film process to produce monolayer, bilayer, or multilayer films. If desired for a given end use, the manufacturer can orient the films by trapped bubble, tenterframe, or other suitable process. Additionally, the manufacturer can optionally anneal the films thereafter.

In one or more implementations, the films of the present invention are blown film, or cast film. Blown film and cast film is formed by extrusion. The extruder used can be a conventional one using a die, which will provide the desired gauge. Some useful extruders are described in U.S. Pat. Nos. 4,814,135; 4,857,600; 5,076,988; 5,153,382, each of which are incorporated herein by reference. Examples of various extruders, which can be used in producing the films to be used with the present invention, can be a single screw type modified with a blown film die, an air ring, and continuous take off equipment.

In a blown film process, the die can be an upright cylinder with an annular opening. Rollers can pull molten plastic upward away from the die. An air-ring can cool the film as the film travels upwards. An air outlet can force compressed air into the center of the extruded annular profile, creating a bubble. The air can expand the extruded circular cross section by a multiple of the die diameter. This ratio is called the "blow-up ratio." When using a blown film process, the manufacturer can collapse the film to double the plies of the film. Alternatively, the manufacturer can cut and fold the film, or cut and leave the film unfolded.

In one implementation, the multi-ply, puckered thermoplastic film comprises a first ply of thermoplastic material having a first ply maximum gauge, wherein the first ply has been cold formation stretched to form alternating thick areas of un-stretched material and thin areas of stretched material; a second ply of thermoplastic material having a second ply maximum gauge and adjacent to the first ply, wherein the second ply has not been cold formation stretched; a plurality of non-continuous laminated areas bonding the first ply to the second ply wherein the laminated areas between the first ply and the second ply are formed with the first ply in the stretched condition; and a plurality of puckers in the second thermoplastic ply, the puckers being located between and maintained by adjacent laminated areas and the puckers having a height of at least 1.25 times the sum of the first ply maximum gauge and the second ply maximum gauge. Cold formation stretching can decrease the gauge and create greater orientation and give improved properties.

In another implementation, the multi-ply, puckered thermoplastic film comprises a first ply of thermoplastic material having a first ply maximum gauge, wherein the first ply has been cold formation stretched by MD ring rolling to form alternating thick layers of un-stretched material and thin areas of stretched material; a second ply of thermoplastic material having a second ply maximum gauge and adjacent to the first ply; a plurality of non-continuous laminated areas bonding thick areas of the first ply to the second ply wherein the laminated areas are formed with the first ply in the stretched condition; and a plurality of puckers in the second thermoplastic ply, the puckers being located between and maintained by adjacent laminated areas and the puckers having a height of at least 1.25 times the sum of the first ply maximum gauge and the second ply maximum gauge.

In another implementation, the multi-ply, puckered thermoplastic film formed from first and second thermoplastic films, comprises a first thermoplastic film ply with a first gauge; a second thermoplastic film ply with a second gauge; a plurality of non-continuous laminated areas that bond the first and the second thermoplastic film plies together wherein the laminated areas are formed with the first ply in the stretched condition; and a plurality of puckers in one or more of the first and the second thermoplastic film plies, the puckers being located between and maintained by adjacent laminated areas; wherein a loft of the puckers is greater than a sum of the first gauge and the second gauge.

Figure 1B:
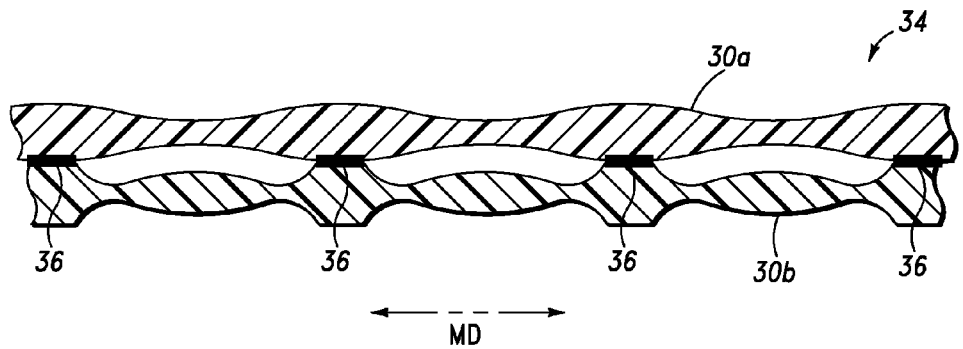
FIG. 1B illustrates a side, cross-sectional view of two thermoplastic films stretched and non-continuously laminated together in accordance with one or more implementations of the present invention.
Figure 1C:
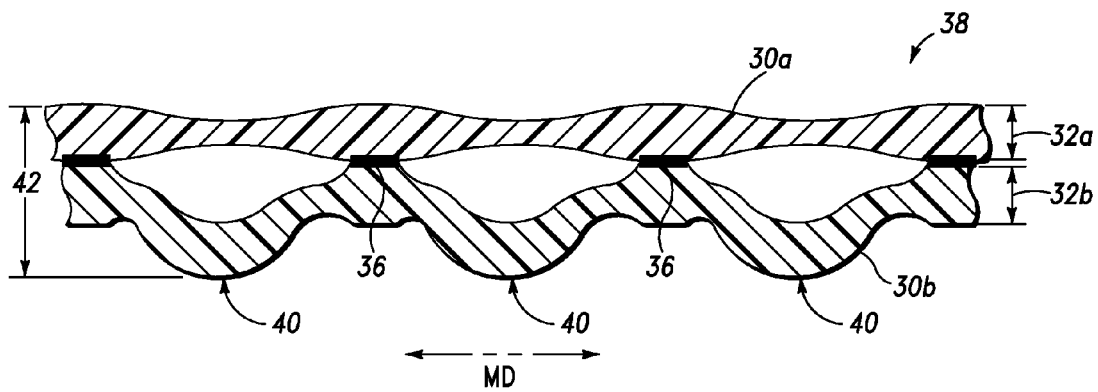
FIG. 1C illustrates a side, cross-sectional view of a multi-ply, puckered thermoplastic film with increased loft in accordance with one or more implementations of the present invention.

Referring now to the Figures, FIGS. 1A-1C illustrate one implementation of a process of stretching, non-continuously laminating, and releasing a multi-ply thermoplastic film to create puckers in the film. As previously mentioned the puckers can increase the loft of the film. For example, in FIG. 1A, 30a represents a film that has been cold formation stretched by MD ring rolling at a small strain and 30b represents a film that has been cold formation stretched MD ring rolling at a larger strain. The film 30a has alternating thick areas 31a and thin areas 31b and a maximum gauge 32a. The film 30b has alternating thick areas 31c, 31d and thin areas 31e, 31f and a maximum gauge 32b. The cold formation stretched MD ring rolled plies 30a, 30b are flexible film plies of thick and thin areas as opposed to rigid fluted structures, which are not suitable for to produce the puckered laminates of the invention.

In particular, FIG. 1A illustrates a first thermoplastic film 30a with a first starting gauge 32a and a second thermoplastic film 30b with a second starting gauge 32b. Together the first and second thermoplastic films 30a, 30b can have an initial loft 32a plus 32b. As used herein, the term "loft" refers to the largest distance between the outer major surfaces of a film. Thus, the combined loft (32a plus 32b) of the first and second thermoplastic films 30a, 30b is equal to the sum of the starting gauge 32a and the starting gauge 32b.

In one or more implementations, prior to stretching and laminating, the starting gauges 32a, 32b need not be consistent or uniform throughout the entirety of the first and second thermoplastic films 30a, 30b. Thus, the starting gauges 32a, 32b can vary along one or both dimensions of the film due to cold formation stretching, intentional product design, manufacturing defects, tolerances, or other processing inconsistencies. The films of one or more implementations of the present invention can have a starting gauge between about 0.1 mils to about 20 mils, suitably from about 0.2 mils to about 4 mils, suitably in the range of about 0.3 mils to about 2 mils, suitably from about 0.6 mils to about 1.25 mils, suitably from about 0.9 mils to about 1.1 mils, suitably from about 0.3 mils to about 0.7 mils, and suitably from about 0.4 mils and about 0.6 mils.

The individual films or plies (e.g., first and second thermoplastic films 30a, 30b) may each themselves comprise a plurality of film layers. Such film layers may be joined by, for example, co-extrusion, spread coating, extrusion coating, and combinations thereof. In particular, one or more of the first and second thermoplastic films 30a, 30b can comprise two, three, four, or more co-extruded, or otherwise bonded, layers. For ease in description, the first and second thermoplastic films 30a, 30b are described and shown herein as single film layers. One will appreciate, however, that the present invention is not so limited, and the first and second thermoplastic films 30a, 30b can each include one, two, three, or more layers.

Additionally, the present invention contemplates using more than two separate thermoplastic films or plies to create multi-ply, puckered thermoplastic films with increased loft. For example, multi-ply, puckered thermoplastic films of one or more implementations can include two, three, or more separate films or plies. Furthermore, one or more of the thermoplastic films or plies can include puckers as explained in greater detail below. For ease in description, multi-ply, puckered thermoplastic films including two film plies (i.e., first and second thermoplastic films 30a, 30b) are described and shown herein. One will appreciate, however, that the present invention is not so limited, and more than two film plies can be stretched, non-continuously laminated, and released to form multi-ply, puckered thermoplastic films.

As alluded to earlier, the first thermoplastic film 30a can have a first rebound ratio and the second thermoplastic film 30b can have a second rebound ratio, differing from the first rebound ratio. As used herein, the term "rebound ratio" refers to how much a film will rebound or snapback after stretching and releasing. In particular, the term "rebound ratio" refers to the ratio of a dimension of the film after stretching and releasing of the film compared to the dimension after stretching. For example, a film that is stretched to a length of 1.25 meters and released, and rebounds, upon release, to a length of about 1.0 meter has a rebound ratio of 0.80 (1.0/1.25).

One will appreciate in light of the disclosure herein that various factors influence the rebound ratio of a thermoplastic film. For example, the elasticity of a thermoplastic film can influence the rebound ratio of the thermoplastic film. Additionally, the amount or degree of stretching the thermoplastic film undergoes can influence the rebound ratio of the thermoplastic film. Thus, two films of the same thermoplastic material can have different rebound ratios if they are stretched to differing degrees. Similarly, two films of different thermoplastic material can have different rebound ratios when stretched to the same degree or differing degrees, depending upon their material properties.

In any event, the first thermoplastic film 30a can have a first rebound ratio and the second thermoplastic film 30b can have a second rebound ratio, differing from the first rebound ratio. A difference in material properties of the first and second thermoplastic films 30a, 30b can provide the difference in rebound ratios. Alternatively, or additionally, a difference in the degree of stretching which the first and second thermoplastic films 30a, 30b undergo can provide the difference in rebound ratios.

As previously mentioned, one or more implementations include stretching one or more of the first and second thermoplastic films 30a, 30b. The two films 30a and 30b can be laminated under stretching tension by MD ring rolling together to give a cold formation stretched film laminate 34 shown in FIG. 1B, where film 30a stretches to a greater extent during lamination than film 30b to give laminated areas 36.

For example, FIG. 1B illustrates the first thermoplastic film 30a stretched to increase its length. A manufacturer can also optionally stretch the second thermoplastic film 30b to the same or differing degree as the first thermoplastic film 30a. Alternatively, the second thermoplastic film 30b can remain unstretched so long as the first and second thermoplastic films 30a, 30b have differing rebound ratios. One will appreciate in light of the disclosure herein that any of MDO, tentering, MD ring rolling, TD ring rolling, diagonal direction ("DD") ring rolling, a structural elastic like film process ("SELFing"), embossing, other stretching methods, or combinations thereof may be used to stretch one or more of the first and second thermoplastic films 30a, 30b.

After stretching one or more of the first and second thermoplastic films 30a, 30b, a manufacturer can non-continuously laminate the first and second thermoplastic films 30a, 30b together. As used herein, the terms "lamination," "laminate," and "laminated film," refer to the process, and resulting product, made by bonding together two or more plies of film or other materials. The term "bonding," when used in reference to bonding of multiple plies of a multi-ply film, may be used interchangeably with "lamination" of the plies. According to methods of one or more implementations of the present invention, adjacent plies of a multi-ply film are non-continuously laminated or bonded to one another.

Non-continuous lamination includes discontinuous lamination and partially discontinuous lamination. Discontinuous lamination refers to lamination of two or more plies where the lamination is not continuous in the machine direction and not continuous in the transverse direction. More particularly, discontinuous lamination refers to lamination of two or more plies with repeating bonded patterns broken up by repeating un-bonded areas in both the machine direction and the transverse direction of the film.

Partially discontinuous lamination refers to lamination of two or more plies where the lamination is substantially continuous in the machine direction or in the transverse direction, but not continuous in the other of the machine direction or the transverse direction. Alternately, partially discontinuous lamination refers to lamination of two or more plies where the lamination is substantially continuous in the width of the article but not continuous in the height of the article, or substantially continuous in the height of the article but not continuous in the width of the article. More particularly, partially discontinuous lamination refers to lamination of two or more plies with repeating bonded patterns broken up by repeating unbounded areas in either the machine direction or the transverse direction.

In order to combine the lamination with an additional stretching operation, it may be advantageous to laminate the two or more plies by a non-heated cold formation process from the group consisting of as MD ring rolling, TD ring rolling, SELFing or combinations thereof. The lamination step may also be performed by an alternative process, such as adhesive lamination or heated or non-heated embossing. In order to preserve the orientation achieved by the prior cold formation stretching operations, it may be advantageous to perform the lamination with the two or more plies aligned in the same direction, such as the MD direction, rather than forming a cross-laminate or laminate where one ply is aligned at an angle to the other ply.

For example, FIG. 1B illustrates the first thermoplastic film 30a partially discontinuously bonded to the second thermoplastic film 30b by a plurality of laminated areas 36, where the lamination takes place after the first thermoplastic film 30a has been stretched to a greater degree than the second thermoplastic film 30b. The first thermoplastic film 30a has lesser rebound ratio than the second thermoplastic film 30b. FIG. 1B shows the thermoplastic films 30a, 30b in the stretched and laminated condition. In particular, the laminated areas 36 extend continuously between the first and second films 30a, 30b in the transverse direction, but non-continuously in the machine direction. As shown by FIG. 1B, the laminated areas 36 are uniformly spaced across the first and second thermoplastic films 30a, 30b. In alternative implementations, the laminated areas 36 can be regularly or irregularly spaced. One will appreciate that the pattern or configuration of the laminated areas 36 can depend upon the technique used to laminate the first and second thermoplastic films 30a, 30b.

A manufacturer can use one or more suitable techniques to non-continuously laminate the first and second thermoplastic films 30a, 30b together. For example, a manufacturer can use pressure without (for example MD ring rolling, TD ring rolling, stainable network lamination, or cold embossing), or a combination of heat and pressure, such as heated embossing. The combination of pressure and heat will normally form a stronger laminate, but will also be a more complicated and expensive process. Alternately, a manufacturer can use ultrasonic bonding. Still further, a manufacturer can use adhesives to laminate the first and second thermoplastic films 30a, 30b together. Treatment with a Corona discharge can enhance the lamination step of any of the above methods.

After lamination, the film laminate 34 is released to a relaxed state, as in FIG. 1C, to give laminate 38 with puckers 40, where the increased loft or height 42 of the puckered laminate 38 is greater than the sum of the gauges 32a, 32b of films 30a and 30b. The height 42 of the puckers 40 can be at least 1.1 times, 1.25 times, 1.5 times, 2 times, more than 2 times, 3 times, or more than 3 times the sum of gauges 32a and 32b.

After lamination, the manufacturer can release the first and second thermoplastic films 30a, 30b to a relaxed state to form a multi-ply, puckered thermoplastic film 38 as shown by FIG. 1C. Upon release, one of the first and the second thermoplastic films 30a, 30b can rebound more than the other of the first and second films 30a, 30b due to the difference in rebound ratios. For example, as shown by FIG. 1C, the second thermoplastic film 30b can rebound more than the first thermoplastic film 30a. The difference in rebound, in connection with the laminated areas 36, can cause the second thermoplastic film 30b to billow between adjacent laminated areas 36, thereby, creating puckers 40.

As used herein the term "pucker" refers to the billowing of a thermoplastic film between non-continuous laminated areas such that the thermoplastic film does not lie in a planar position between adjacent laminated areas. One will appreciate that a pucker, as used herein, is created by the drawing together of adjacent laminated areas 36 formed when a stretched film 30a is non-continuously laminated at laminated areas 36 to an adjacent film 30b thereby forming puckers 40 in the adjacent film 30b. Thus, in one or more implementations, the puckers 40 are formed and maintained by a strain or force (e.g., laminated areas 36) external to the puckered film (e.g., second thermoplastic film 30b). In other words, in one or more implementations, a pucker is not a structure or geometry imparted or formed into a film that will retain its shape or geometry when the puckered film is no longer subject to any external strains or forces, for example, as in a corrugated or fluted film. Thus, in one or more implementations, puckers also differ from ribs or other structures imparted or formed in a film during SELFing, ring rolling, embossing, or other similar processes that retain their form when the film is no longer subject to any strains or externally applied forces.

Thus, the multi-ply, puckered thermoplastic film 38 can include a first thermoplastic film ply (first thermoplastic film 30a) and a second thermoplastic film ply (second thermoplastic film 30b). A plurality of non-continuous laminated areas 36 can bond the first and the second thermoplastic film plies 30a, 30b of the multi-ply, puckered thermoplastic film 38 together. Furthermore, the second thermoplastic film ply 30b can include a plurality of puckers 40 located between and maintained by adjacent laminated areas 36.

The puckers 40 can increase the loft 42 of multi-ply, puckered thermoplastic film 38 compared to the loft 32a and 32b of the first and second thermoplastic films 30a, 30b. In particular, the loft 42 of the multi-ply, puckered thermoplastic film 38 can be between 1.1 and about 20 times, or between 1.1 and 200 times, or 1.1 and 500 times greater than the loft 32a plus 32b of the first and second thermoplastic films 30a, 30b. Suitably, the loft 42 of the multi-ply, puckered thermoplastic film 38 is between about 1.1 and about 10 times greater than the loft 32a plus 32b of the first and second thermoplastic films 30a, 30b. In additional implementations, the loft 42 of the multi-ply, puckered thermoplastic film 38 is between about 1.25 and about 5 times greater than the loft 32a plus 32b of the first and second thermoplastic films 30a, 30b. In further implementations, the loft 42 of the multi-ply, puckered thermoplastic film 38 is about 1.50, about 2, about 2.5, about 3, or about 4 times greater than the loft 32a plus 32b of the first and second thermoplastic films 30a, 30b. In other implementations, the loft 42 of the multi-ply, puckered thermoplastic film 38 is about greater than 10 times, or 20 times, or 50 times, or 100 times the loft 32a plus 32b of the first and second thermoplastic films 30a, 30b.

The increased loft 42 of the multi-ply, puckered thermoplastic film 38 can provide the film 38 with a look and a feel of a stronger film. In particular, the increased loft can connote increased strength to a consumer. In addition to the differences in loft, the space between the first and the second thermoplastic films 30a, 30b created by the puckers 40 can scatter light and make the multi-ply, puckered thermoplastic film 38 less transparent or translucent. By increasing the opacity, the puckers 40 can make the multi-ply, puckered thermoplastic film 38 appear thicker.

One will appreciate in light of the disclosure herein that the pattern of the puckers can vary depending on the method used to stretch and/or laminate the thermoplastic films. For example, in FIG. 1A, 30a represents a film that has been cold formation stretched by MD ring rolling at a small strain and 30b represents a film that has been cold formation stretched MD ring rolling at a larger strain. The film 30a has alternating thick areas 31a and thin areas 31b and a maximum gauge 32a. The film 30b has alternating thick areas 31c, 31d and thin areas 31e, 31f and a maximum gauge 32b. The two films 30a and 30b are then laminated under tension by MD ring rolling together to give a stretched film laminate 34 shown in FIG. 1B, where film 30a stretches to a greater extent during lamination than film 30b to give laminated areas 36. After lamination, the film laminate 34 is relaxed, as in FIG. 1C, to give laminate 38 with puckers 40, where the increased loft or height 42 of the puckered laminate 38 is greater that the sum of the gauges 32a, 32b of films 30a and 30b. The height 42 of the puckers 40 can be at least 1.1 times, 1.25 times, 1.5 times, 2 times, more than 2 times, 3 times, or more than 3 times the sum of gauges 32a and 32b.

Figure 2A:
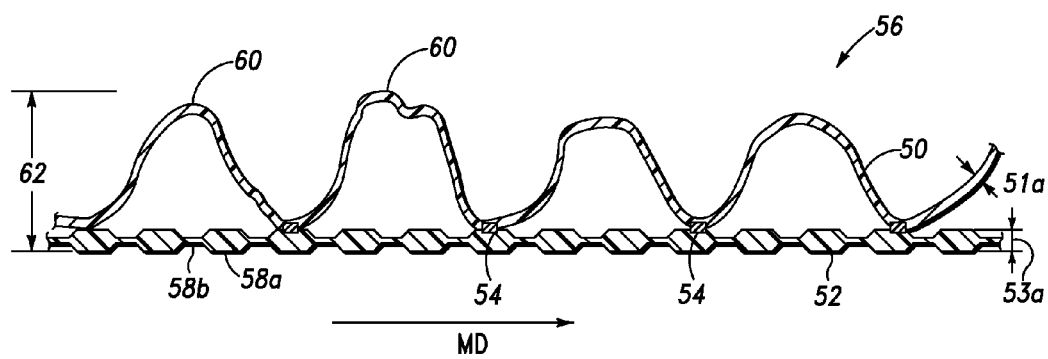
FIG. 2A illustrates a side, cross-sectional view of two thermoplastic films stretched and laminated together in accordance with one or more implementations of the present invention.

FIG. 2A illustrates a side view of a flat film ply 50 laminated to cold formation stretched film ply 52 at laminated areas 54 to give laminated multi-ply film 56. The film ply 52 was cold formation stretched by MD ring rolling to give alternating thick areas 58a and thin areas 58b. Alternately, the film ply could be cold formation stretched by another process such as TD ring rolling or strainable network formation to give thick areas and thin areas. Film ply 52 has a maximum gauge of 53a. Film ply 50 has a relatively constant gauge 51a and is relatively flat. The multi-ply film 56 has puckers 60 with the height 62 of the puckers 60 is greater than the sum of the gauges 51a and 53a of the film plies 50, 52. The height of the puckers can be at least 1.1 times, 1.25 times, 1.5 times, 2 times, more than 2 times, 3 times, or more than 3 times the sum of gauges 51a and 51b.

Figure 2B:
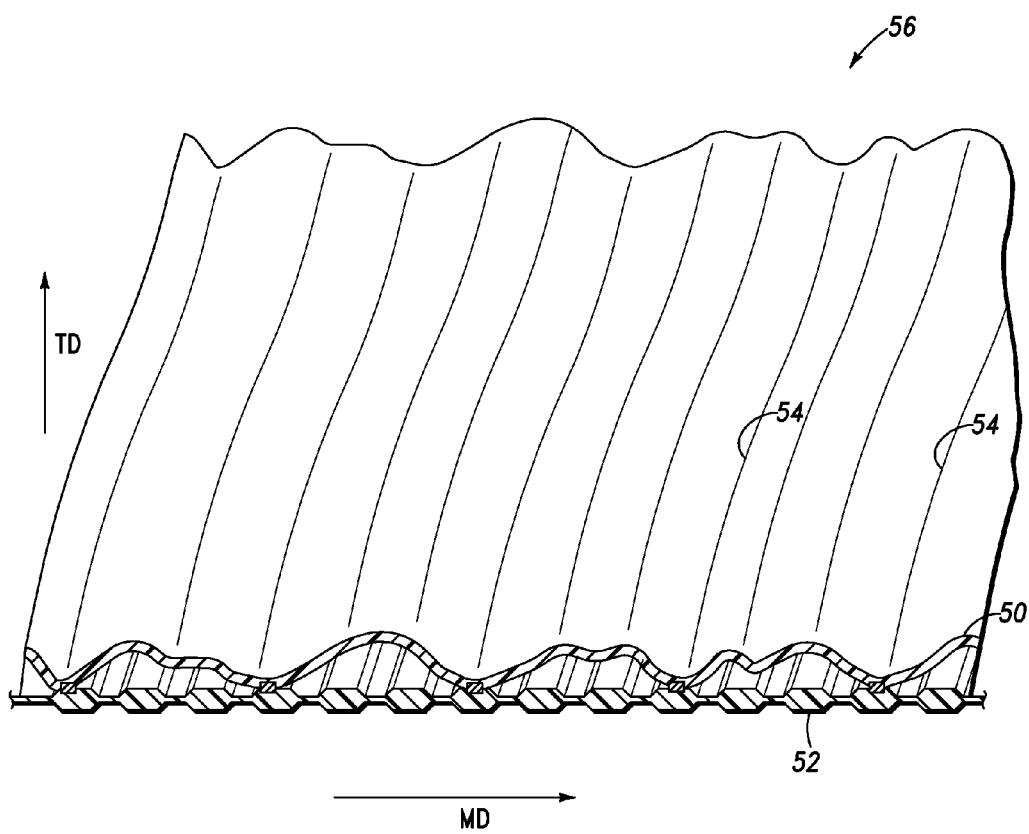
FIG. 2B illustrates a perspective view of two thermoplastic films of FIG. 3A stretched and partially non-continuously laminated together in accordance with one or more implementations of the present invention.

FIG. 2B illustrates a perspective view of a flat film ply 50 laminated to cold formation stretched film ply 52 at laminated areas 54 to give laminated multi-ply film 56. The laminated areas 54 are continuous in the TD direction, but discontinuous in the MD direction to give partially discontinuous lamination. The lamination areas were formed by a cold formation process selected from the group consisting of MD ring rolling, TD ring rolling, and strainable network formation, or combinations thereof. The cold formation process may advantageously result in additional cold stretching. The lamination areas could also be formed by a non-cold formation process such as embossing or adhesive bonding.

Figure 3A:
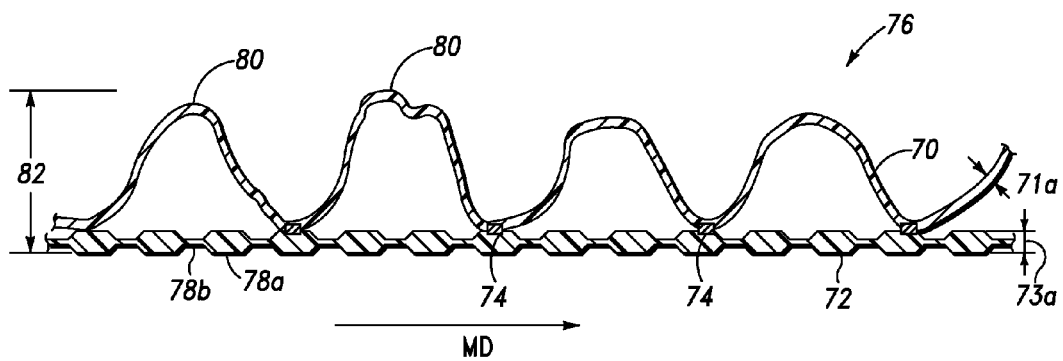
FIG. 3A illustrates a side, cross-sectional view of two thermoplastic films stretched and laminated together in accordance with one or more implementations of the present invention.

FIG. 3A illustrates a side view of a flat film ply 70 laminated to cold formation stretched film ply 72 at laminated areas 74 to give laminated multi-ply film 76. The film ply 72 was cold formation stretched by MD ring rolling to give alternating thick areas 78a and thin areas 78b. Alternately, the film ply could be cold formation stretched by another process such as TD ring rolling or strainable network formation to give thick areas and thin areas. Film ply 72 has a maximum gauge of 73a. Film ply 70 has a relatively constant gauge 71a and is relatively flat. The multi-ply film 76 has puckers 80 with the height 82 of the puckers 80 is greater than the sum of the gauges 71a and 73a of the film plies 70, 72. The height of the puckers can be at least 1.1 times, 1.25 times, 1.5 times, 2 times, more than 2 times, 3 times, or more than 3 times the sum of gauges 71a and 71b. The lamination was formed with both film plies oriented in the MD direction, rather than as a cross laminate.

Figure 3B:
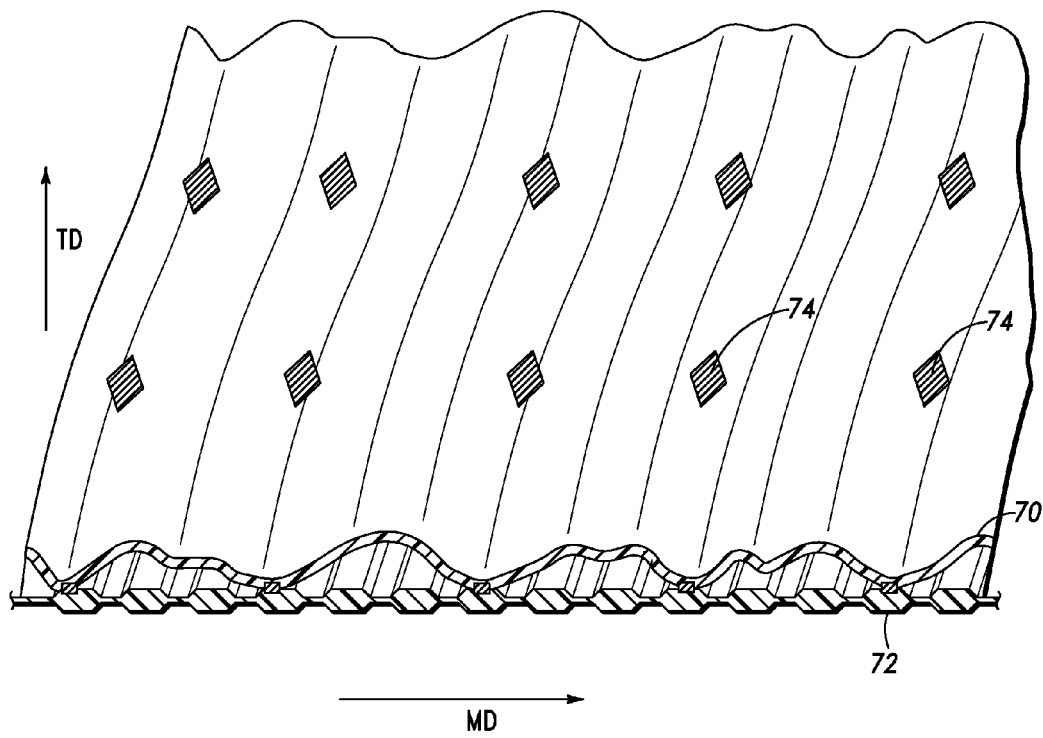
FIG. 3B illustrates a perspective view of two thermoplastic films of FIG. 3A stretched and non-continuously laminated together in accordance with one or more implementations of the present invention.

FIG. 3B illustrates a perspective view of a flat film ply 70 laminated to cold formation stretched, MD ring rolled film ply 72 at laminated areas 74 to give laminated multi-ply film 76. The laminated areas 74 are discontinuous in the TD direction and discontinuous in the MD direction. The lamination areas were formed by a process selected from the group consisting of MD ring rolling, TD ring rolling, strainable network formation, embossing, adhesive bonding, or combinations thereof. The lamination was formed with both film plies oriented in the MD direction, rather than as a cross laminate.

Figure 4:
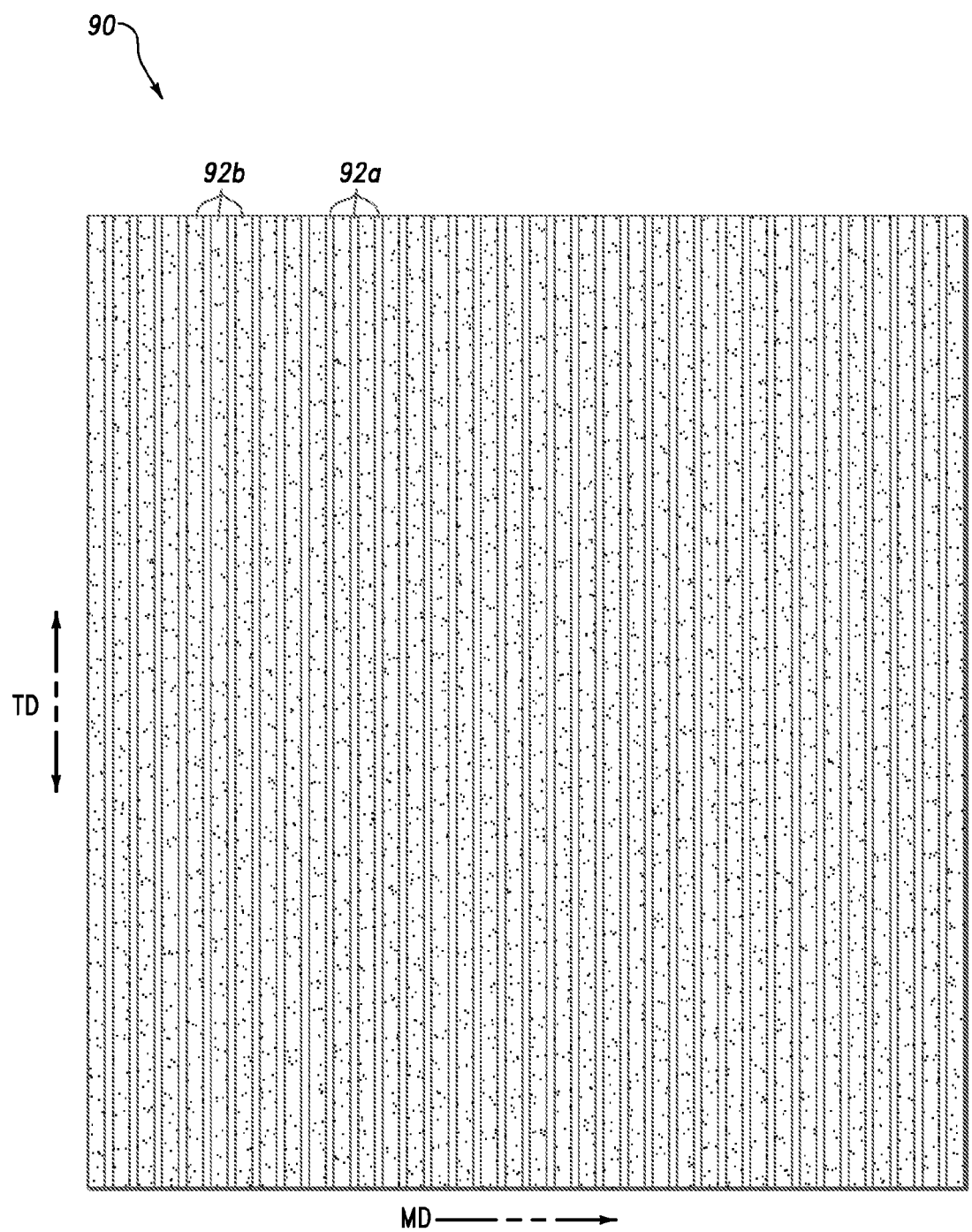
FIG. 4 illustrates a top view of a multi-ply, puckered thermoplastic film with increased loft formed using MD ring rolling in accordance with one or more implementations of the present invention.

FIG. 4 illustrates a top view of a multi-ply, puckered thermoplastic film 90 in which the plies of the film 90 oriented in the MD direction and were partially discontinuously laminated together using MD ring rolling under conditions where the plies of the film 90 had different rebound ratios. As shown by FIG. 4, the film 90 can include alternating puckers 92a and laminated areas 92b. Further, either or both of the puckers 92a and the "un-puckered" laminated areas 92b can extend along the length of the film in the transverse direction.

When ring rolling is used for stretching and laminating, the pitch (distance between adjacent teeth or ridges on the ring rolls) and the depth of engagement ("DOE") (overlap of intermeshing teeth or ridges of the ring rolls) can determine the width and spacing of the puckers and/or laminated areas. By varying the pitch and/or DOE of the ring rolls, a manufacturer can vary the width and/or spacing of the puckers. Thus, a manufacturer can impart a rougher feel to a multi-ply, puckered thermoplastic film by increasing the frequency and/or reducing the size of the puckers. Alternatively, a manufacturer can impart a softer feel to a multi-ply, puckered thermoplastic film by decreasing the frequency and/or increasing the size of the puckers.

FIG. 4 further illustrates that the puckers 92a can reside about un-puckered laminated areas 92b. In particular, each pucker 92a can reside between adjacent laminated areas 92b. Additionally, the puckers 92a can have a distinct feel or look compared with the laminated areas 92b. In particular, the puckers 92a can differ from the laminated areas 92b in one or more of feel or look. For example, the puckers 92a can feel thicker and look more opaque than the laminated areas 92b.

The loft of the puckers of one or more implementations can vary based on the rebound ratio of the plies within the multi-ply, puckered thermoplastic film. For instance, when the multi-ply, puckered thermoplastic film contains two film plies with small differences in rebound ratios, the loft of the puckers may be relatively small. On the other hand, when the multi-ply, puckered thermoplastic film contains two film plies with large differences in rebound ratios, the loft of the puckers can be relatively large.

Figure 5:
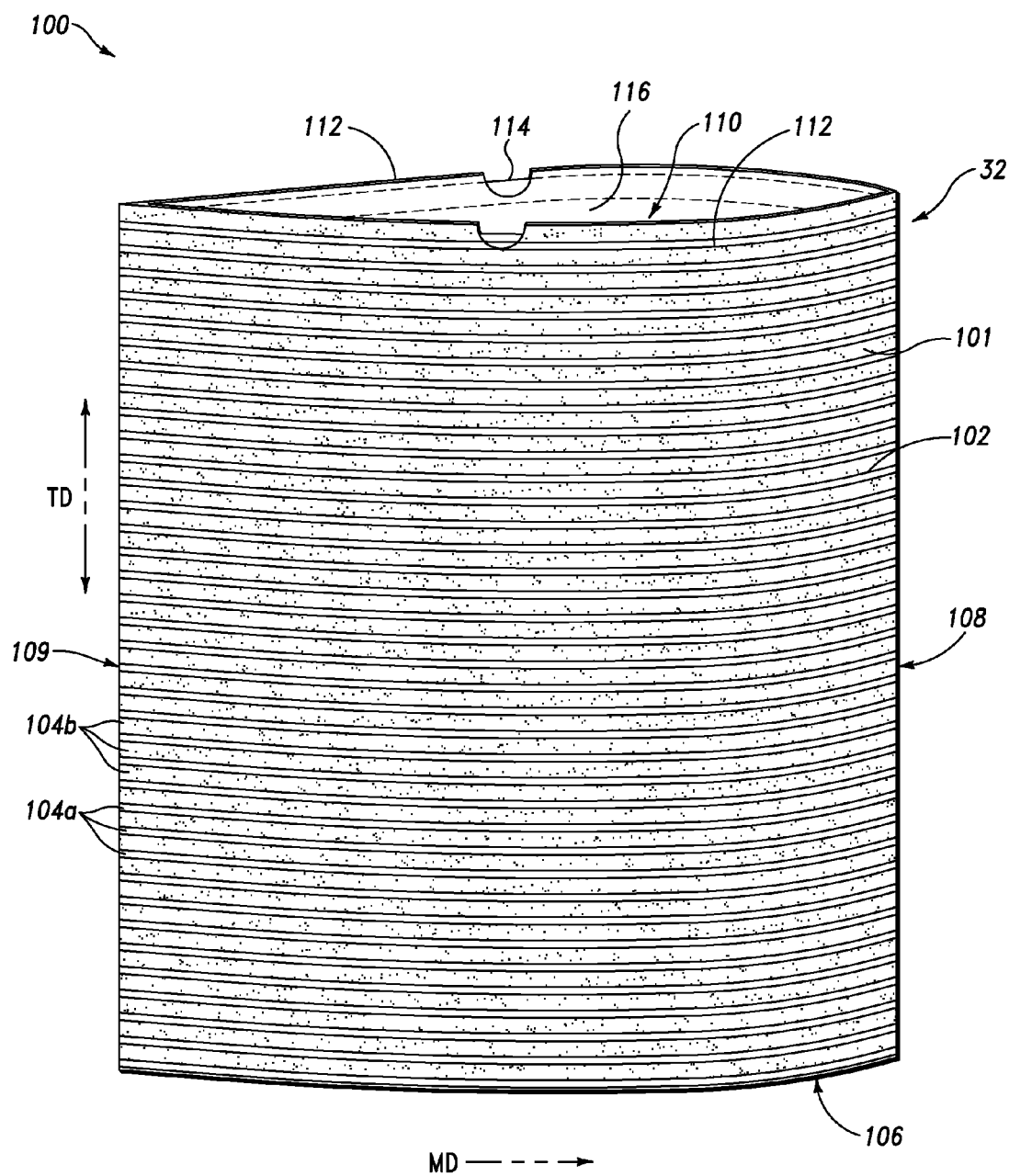
FIG. 5 illustrates a perspective view of a bag having a multi-ply, puckered thermoplastic film with increased loft formed using TD ring rolling in accordance with one or more implementations of the present invention.

As mentioned previously, MD ring rolling is one exemplary method of stretching and/or laminating thermoplastic films to create a multi-ply, puckered thermoplastic film in accordance with the present invention. TD ring rolling is another suitable method of stretching and/or laminating thermoplastic films to create multi-ply, puckered thermoplastic films. For example in FIG. 5, a perspective view of a bag 100 from a multi-ply, puckered thermoplastic film 102 created by orienting two or more plies in the MD direction, stretching, partially non-continuously laminating via TD ring rolling, and releasing two or more film plies. The multi-ply bag 100 can include a bag body 101 formed from a piece of the multi-ply, puckered thermoplastic film 102 folded upon itself along a bag bottom 106. Side seams 108 and 109 can bond the sides of the bag body 101 together to form a semi-enclosed container having an opening 110 along an upper edge 112. The bag 100 optionally includes closure means located adjacent to the upper edge 112 for sealing the top of the bag 100 to form a fully-enclosed container or vessel. For example, FIG. 5 illustrates that the bag 100 can include a draw tape closure means 114 within a hem 116. In alternative implementations, the closure means can comprise flaps, adhesive tapes, a tuck and fold closure, an interlocking closure, a slider closure, a zipper closure or other closure structures known to those skilled in the art for closing a bag.

As shown by FIG. 5, the multi-ply, puckered thermoplastic film 102 can include alternating puckers 104a and laminated areas 104b. FIG. 5 illustrates that the puckers 104a can extend across the multi-ply, puckered thermoplastic film 102 in the machine direction. As shown by FIG. 5, the puckers 104a can extend across the entire width of the multi-ply, puckered thermoplastic film 102. In alternative implementations, the puckers 104a can extend across only a portion of the multi-ply, puckered thermoplastic film 102. Similar to MD ring rolling, the pitch and the DOE of the TD ring rolls can determine the width and spacing of the puckers 104a.

The shape, size, and/or pattern of the puckers can vary depending upon the method used to stretch and/or laminate the various plies. For example, in one or more implementations MD ring rolling, TD ring rolling, DD ring rolling, SELFing, embossing, or combinations thereof can create puckers with shapes including, but are not limited to, intermeshing circles, squares, diamonds, hexagons, or other polygons and shapes. Additionally, one or more implementations can include puckers arranged in patterns that are combinations of the illustrated and described patterns/shapes.

One will appreciate in light of the disclosure herein that the multi-ply, puckered thermoplastic films can form part of any type of product made from, or incorporating, thermoplastic films. For instance, grocery bags, trash bags, sacks, packaging materials, feminine hygiene products, baby diapers, adult incontinence products, sanitary napkins, bandages, food storage bags, food storage containers, thermal heat wraps, facial masks, wipes, hard surface cleaners, and many other products can include multi-ply, puckered thermoplastic films to one extent or another. Trash bags and food storage bags may be particularly benefited by the films of the present invention.

As previously mentioned, the size, shape, and pattern of the puckers can vary depending upon the method used to stretch and/or laminate the films of a multi-ply, puckered thermoplastic film. For example, in accordance with another implementation, a structural elastic like film (SELF) process may be used to create a multi-ply, puckered thermoplastic film. U.S. Pat. No. 5,518,801; U.S. Pat. No. 6,139,185; U.S. Pat. No. 6,150,647; U.S. Pat. No. 6,394,651; U.S. Pat. No. 6,394,652; U.S. Pat. No. 6,513,975; U.S. Pat. No. 6,695,476; U.S. Patent Application Publication No. 2004/0134923; and U.S. Patent Application Publication No. 2006/0093766 each disclose processes for forming strainable networks or patterns of strainable networks suitable for use with implementations of the present invention. The contents of each of the aforementioned patents and publications are incorporated in their entirety by reference herein.

Figure 6A:
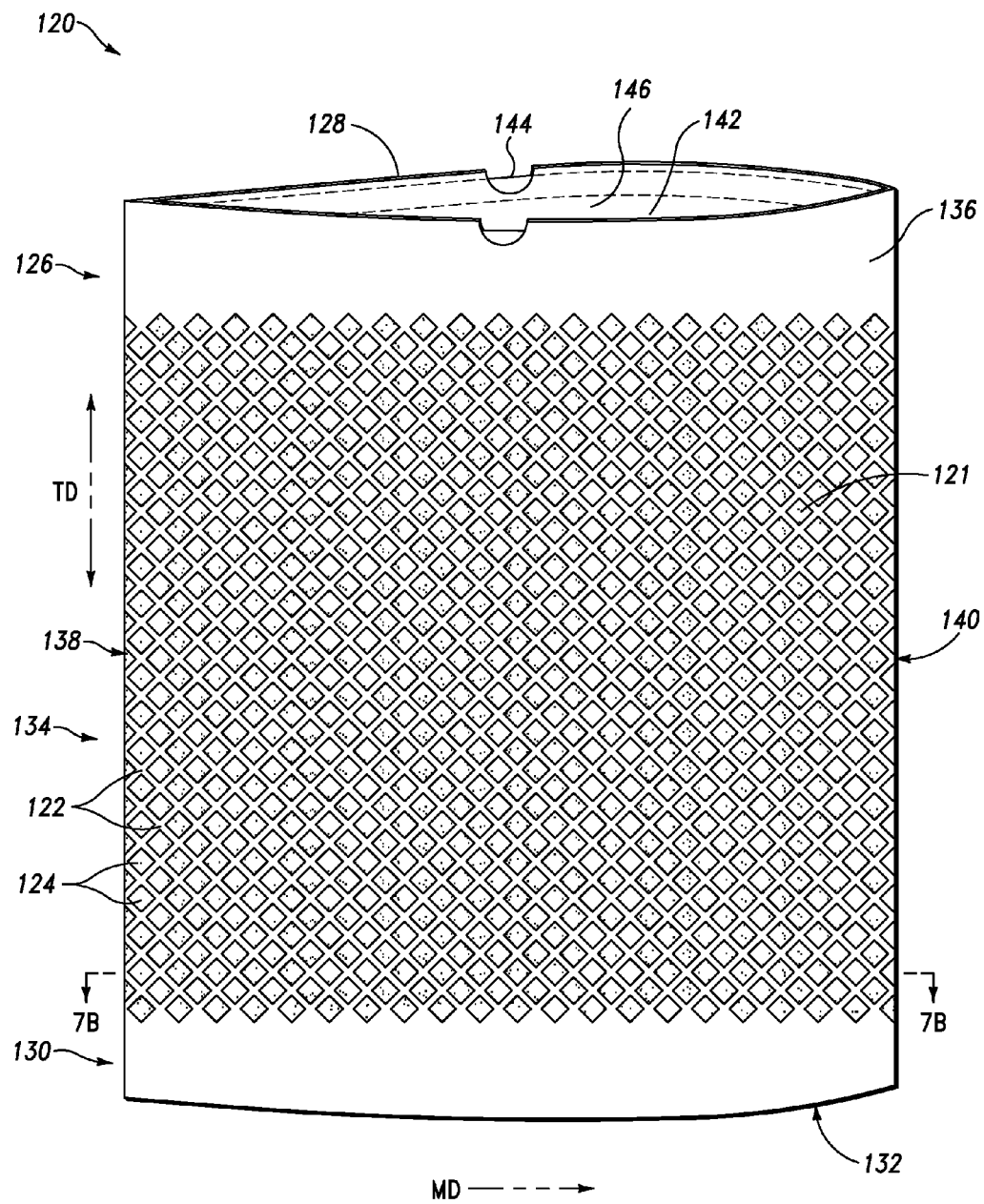
FIG. 6A illustrates a perspective view of a bag incorporating a multi-ply, puckered thermoplastic film similar to the film shown in FIG. 6 in accordance with one or more implementations of the present invention.

For example, FIG. 6A illustrates a view of another multi-ply, puckered bag 120, similar to the bag 100 of FIG. 5, albeit that the bag 120 is formed from a multi-ply, puckered film formed using a SELFing lamination process. As shown by FIG. 6A, the multi-ply, puckered bag 120 can include diamond-shaped laminated areas 122. The multi-ply, puckered film 121 of the bag 120 can further include diamond-shaped puckers 124 surrounding the laminated areas 122. The puckers 124 can increase the loft of the multi-ply, puckered bag 100.

The diamond shape laminated areas 122 can comprise raised rib-like elements of the strainable network. The rib-like elements of the laminated areas 122 can allow the multi-ply, puckered film 121 of the bag 120 to undergo a substantially "geometric deformation" prior to a "molecular-level deformation." As used herein, the term "molecular-level deformation" refers to deformation which occurs on a molecular level and is not discernible to the normal naked eye. That is, even though one may be able to discern the effect of molecular-level deformation, e.g., elongation or tearing of the film, one is not able to discern the deformation which allows or causes it to happen. This is in contrast to the term "geometric deformation," which refers to deformations of the multi-ply, puckered film 121 of the bag 120 which are generally discernible to the normal naked eye when subjected to an applied strain. Types of geometric deformation include, but are not limited to bending, unfolding, and rotating.

Thus, upon application of strain, the rib-like elements of the diamond-shaped laminated areas 122 can undergo geometric deformation before either the rib-like elements 123 of the laminated areas 122 or the puckered regions 124 undergo molecular-level deformation. For example, an applied strain can pull the rib-like elements 123 of the laminated areas 122 back into plane prior to any molecular-level deformation of the multi-ply, puckered film 121 of the bag 120. Geometric deformation can result in significantly less resistive forces to an applied strain than that exhibited by molecular-level deformation.

One or more implementations can include strainable network patterns and resultant puckers other than those shown by FIG. 6A, or combinations of various patterns. It should be understood that the term "pattern" is intended to include continuous or discontinuous sections of patterns, such as may result, for example, from the intersection of first and second patterns with each other. Furthermore, the patterns can be aligned in columns and rows aligned in the machine direction, the transverse direction, or neither the machine or transverse directions.

In addition to the varying the pattern of puckers in a bag or film, one or more implementations also include providing puckers in certain sections of a bag or film, and regions without puckers in other sections of the bag or film. For example, the multi-ply, puckered bag 120 of FIG. 6A includes an upper section 126 adjacent the top edge 128 that is devoid of puckers. Similarly, the multi-ply, puckered bag 120 includes a bottom section 130 adjacent the bottom fold or edge 132 devoid of puckers. In other words, both the top section 126 and bottom section 132 of the multi-ply, puckered bag 120 can each comprise regions without increased loft. The sections 126 and 130 can additionally each have plies that are laminated together or not laminated together. The individual plies of the multi-ply bag 120 can each be stretched before lamination (by MD ring rolling or other stretching processes) or un-stretched before lamination.

A middle section 134 of the multi-ply, puckered bag 120 located between the upper and lower sections 126, 130 on the other hand can include puckers. In particular, FIG. 6A illustrates that the middle section 134 can include diamond-shaped puckers 124 surrounding diamond-shaped laminated areas 122. Thus, the middle section 134 of the multi-ply, puckered bag 120 can include improved properties, such as elasticity and impact resistance, created by the strainable network in addition to the increased loft provided by the puckers 124.

The multi-ply bag 120 can include a bag body 136 formed from a piece of the multi-ply, puckered thermoplastic film 121 folded upon itself along a bag bottom 132. Side seams 138 and 140 can bond the sides of the bag body 136 together to form a semi-enclosed container having an opening 142 along an upper edge 128. The bag 120 optionally includes closure means located adjacent to the upper edge 128 for sealing the top of the bag 120 to form a fully-enclosed container or vessel. For example, FIG. 6A illustrates that the bag 120 can include a draw tape closure means 144 within a hem 146. In alternative implementations, the closure means can comprise flaps, adhesive tapes, a tuck and fold closure, an interlocking closure, a slider closure, a zipper closure or other closure structures known to those skilled in the art for closing a bag.

Thus, one will appreciate in light of the disclosure herein that a manufacturer can tailor specific sections or zones of a bag or film with desirable properties by MD, TD, or DD ring rolling, SELF'ing, embossing or a combination thereof. Furthermore, the configuration of the puckers can serve to notify a consumer of the properties of the different sections. One will appreciate in light of the disclosure herein that the puckered regions with increased loft can feel and/or look more discernable than any geometric deformation alone.

Figure 6B:
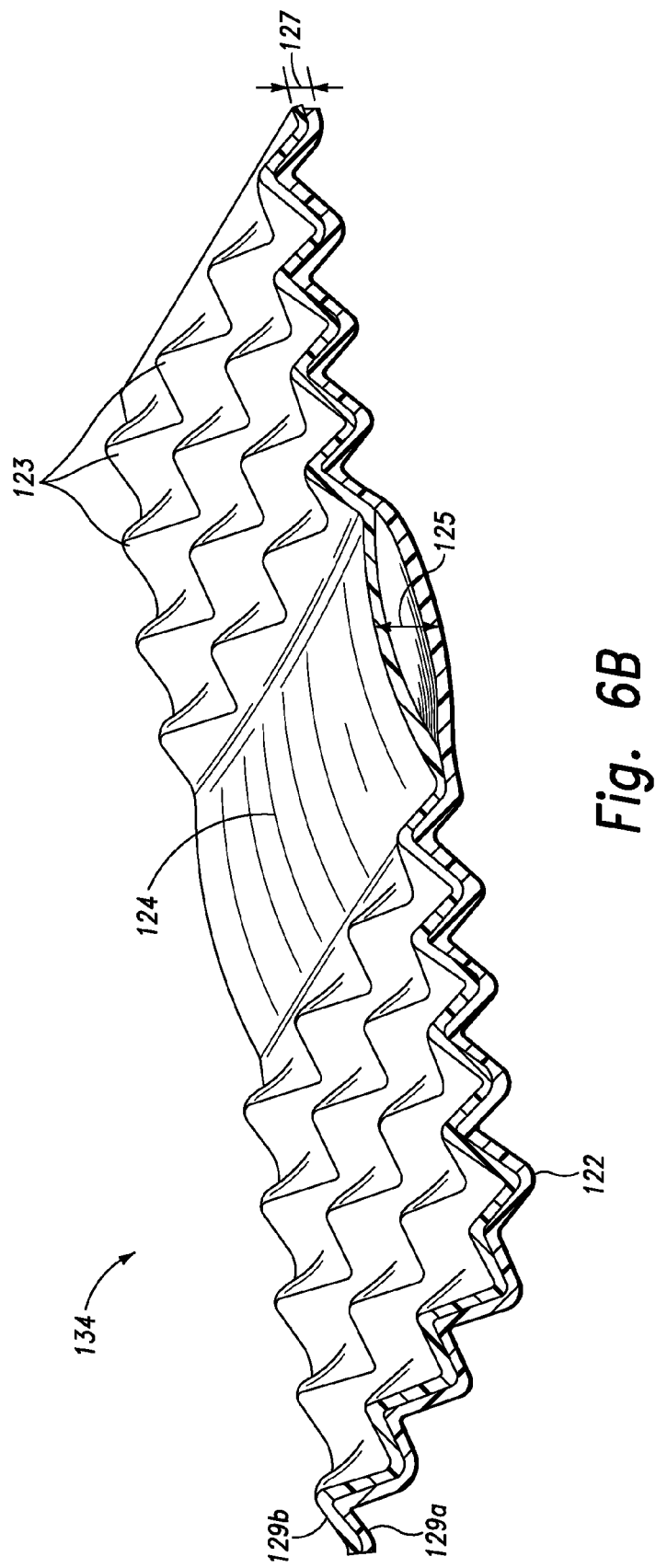
FIG. 6B illustrates a perspective, cross-sectional view of the laminated areas of the multi-ply film of FIG. 6A.

As shown in FIG. 6B, a cross-section of the middle section 134 of the multi-ply film 121 along 6B of FIG. 6A showing film plies 129a and 129b. In one embodiment, one film ply 129a has been cold formation stretched prior to lamination and the other film ply 129b has not been cold formation stretched. In another embodiment, both film plies 129a, 129b have been cold formation stretched prior to lamination, however, film plies 129a, 129b have different rebound ratios. The section 134 shows alternating laminated areas 122 and non-bonded puckered area 124 having a height 125. The laminated areas 122 have rib-like elements 123 with a height 127 that is the sum of the heights of the individual plies 129a and 129b. The height 125 of the puckers 124 can be at least 1.1 times, 1.25 times, 1.5 times, 2 times, more than 2 times, 3 times, or more than 3 times the sum of gauges 127 of the individual plies 192a and 192b.

Figure 7:
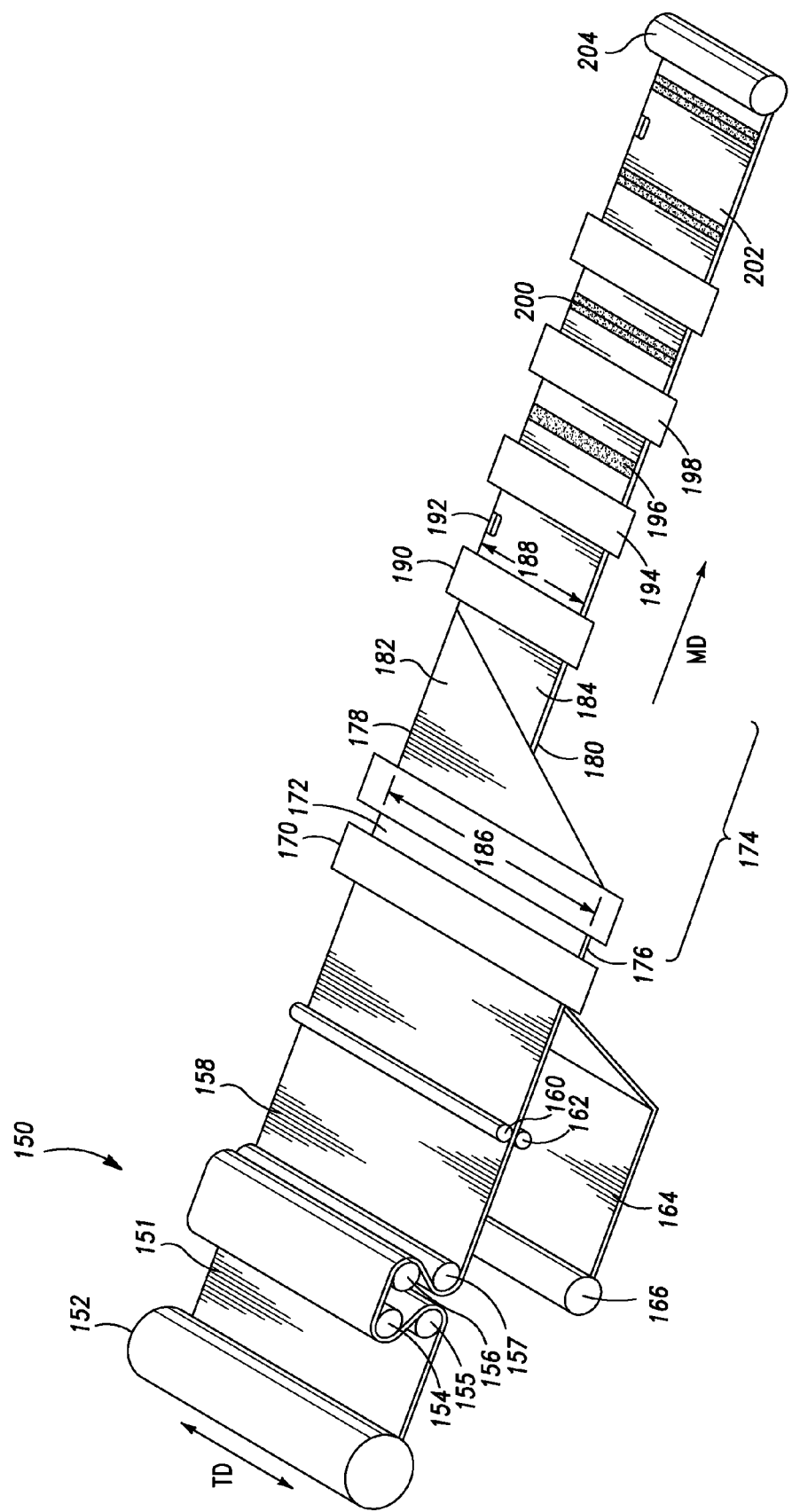
FIG. 7 illustrates a schematic diagram of a bag manufacturing process in accordance with one or more implementations of the present invention.
Figure 8:
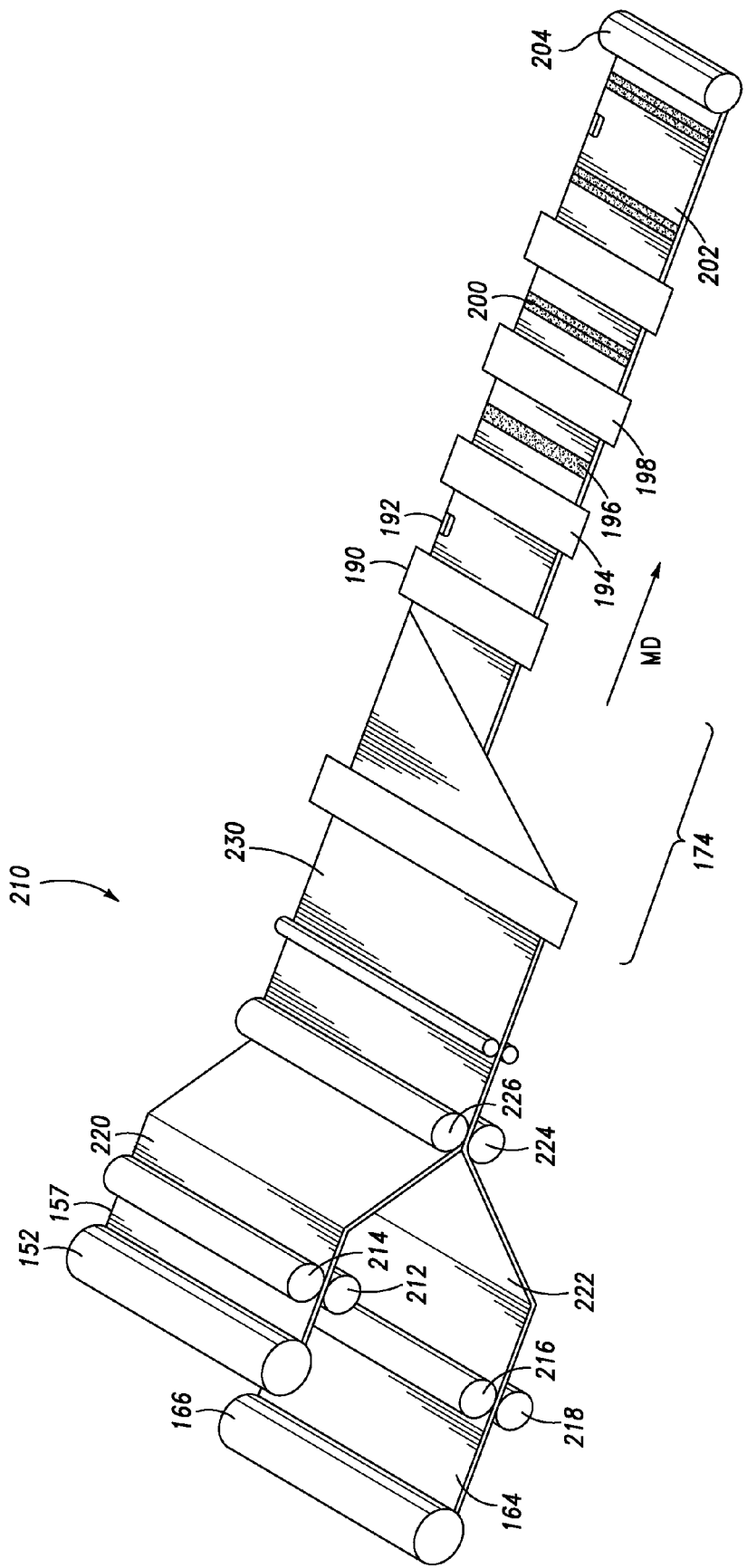
FIG. 8 illustrates a schematic diagram of another bag manufacturing process in accordance with one or more implementations of the present invention.

Implementations of the present invention can also include methods of forming multi-ply, puckered films and bags including the same. FIGS. 7-8 and the accompanying description describe such methods. Of course, as a preliminary matter, one of ordinary skill in the art will recognize that the methods explained in detail herein can be modified. For example, various acts of the method described can be omitted or expanded, additional acts can be included, and the order of the various acts of the method described can be altered as desired.

FIG. 7 illustrates an exemplary embodiment of a high-speed manufacturing process 150 for forming a multi-ply, puckered film with increased loft and producing a plastic bag there from. According to the process 150, a first thermoplastic film 151 is unwound from a roll 152 and directed along a machine direction. The first thermoplastic film 151 is then stretched. For example, the first thermoplastic film 151 can pass about a first set of rollers 154, 155 and a second set of rollers 156, 157 to continuously stretch the first thermoplastic film 151 in the machine direction. In one or more implementations, the first set of rollers 154, 155 and a second set of rollers 156, 157 are not heated and the first thermoplastic film 151 is cold formation stretched under cold or ambient conditions.

The first and second sets of rollers 154, 155, 156, 157 can each have a generally cylindrical shape. The rollers 154, 155, 156, 157 may be made of cast and/or machined metal, such as, steel, aluminum, or any other suitable material. One or more of the rollers may be coated with a material such as a rubber or urethane to improve gripping of the film and to reduce slippage. The rollers 154, 155 of the first set of rollers can rotate in opposite directions about parallel axes of rotation. In further implementations, the first thermoplastic film 151 can pass through MD ring rolls, TD ring rolls, DD ring rolls, SELFing, or embossing rollers.

The first set of rollers 154, 155 can rotate at a first velocity, and the second set of rollers 156, 157 can rotate at a velocity between about 1.1 and about 2.5 times greater than the velocity of the first set of rollers 154, 155. In various implementations, motors may be provided that power rotation of the rollers 154, 155, 156, 157 in a controlled manner. The velocity difference between the first and second sets of the rollers can continuously stretch the first thermoplastic film 151 to create a stretched thermoplastic film 158. The stretching the first thermoplastic film 151 can thin and/or adjust the rebound ratio of the first thermoplastic film 151.

During the manufacturing process 150, the stretched thermoplastic film 158 can pass through a pair of pinch rollers 160, 162. The pinch rollers 160, 162 can grasp the stretched thermoplastic film 158. The pinch rollers 160, 162 may help maintain strain on the stretched thermoplastic film 158.

Additionally, a second thermoplastic film 164 is unwound from a roll 166 and directed along a machine direction. The second thermoplastic film 164 can be un-stretched as shown in FIG. 8. In alternative implementations, the second thermoplastic film 164 can pass through first and second sets of rollers 154, 155, 156, 157 to continuously stretch the second thermoplastic film 164. In further implementations, the second thermoplastic film 164 can pass through MD ring rolls, TD ring rolls, DD ring rolls, SELFing, or embossing rollers.

In any event, the second thermoplastic film 164 is combined with the stretched thermoplastic film 158. The stretched thermoplastic film 158 has a first rebound ratio and the second thermoplastic film 164 has a second rebound ratio, differing from the first rebound ratio. The difference in rebound ratios can be due to a difference in material properties or degree of stretching.

A lamination operation 170 can non-continuously laminate the stretched thermoplastic film 158 and the second thermoplastic film 164 together. Lamination operation 170 can non-continuously laminate the films 158, 164 together via adhesive bonding, pressure bonding, ultrasonic bonding, corona lamination, and the like. Alternatively, lamination operation can non-continuously laminate the films 158, 164 together by passing them through MD ring rolls, TD ring rolls, DD ring rolls, SELF'ing rollers, embossing rollers, or other intermeshing rollers. In any event, the lamination operation 170 can form a plurality of non-continuous lamination areas between the films 158, 164.

After passing through the lamination operation 170, tension in the films 158, 164 is released; thereby, creating a multi-ply, puckered film 172. Alternatively, the tension can be released after a bag is produced. A folding operation 174 can fold the multi-ply, puckered film 172 to produce the sidewalls of the finished bag. In particular, the folding operation 174 can move a first edge 176 adjacent to the second edge 178, thereby creating a folded edge 180. The folding operation 174 thereby provides a first film half 182 and an adjacent second web half 184. The overall width 188 of the second film half 184 can be half of the width 186 of the pre-folded multi-ply, puckered film 172.

To produce the finished bag, the processing equipment may further process the folded multi-ply, puckered film 172. In particular, a draw tape operation 190 can insert a draw tape 192 into the multi-ply, puckered film 172. Furthermore, a sealing operation 194 can form the parallel side edges of the finished bag by forming heat seals 196 between adjacent portions of the multi-ply, puckered film 172. The sealing operation 194 can space the heat seals 196 along the folded multi-ply, puckered film 172. The sealing operation 194 can form the heat seals 196 using a heating device, such as, a heated knife.

A perforating operation 198 may form a perforation 200 in the heat seals 196 using a perforating device, such as, a perforating knife. The perforations 200 in conjunction with the folded outer edge 180 can define individual bags 202 that may be separated from the multi-ply, puckered film 172. A roll 204 can wind the multi-ply, puckered film 172 embodying the finished multi-ply, puckered bags 202 for packaging and distribution. For example, the roll 204 may be placed into a box or bag for sale to a customer.

In still further implementations, the folded multi-ply, puckered film 172 may be cut into individual bags along the heat seals 196 by a cutting operation. In another implementation, the folded multi-ply, puckered film 172 may be folded one or more times prior to the cutting operation. In yet another implementation, the side sealing operation 194 may be combined with the cutting and/or perforation operations 198.

FIG. 8 illustrates yet another manufacturing process 210 for producing multi-ply, puckered films and bags including the same. The process 210 can be similar to process 150 of FIG. 8, except that the first and second thermoplastic films 151, 164 each are incrementally stretched and then non-continuously laminated together. According to the process 210, a first thermoplastic film 151 and a second thermoplastic film 164 are unwound from rolls 152, 166 and directed along a machine direction.

The process 210 can then include incrementally stretching one or more of the first and second thermoplastic films 151, 164. For example, the first thermoplastic film 151 can pass between first and second cylindrical intermeshing rollers 212, 214 to incrementally stretch and/or modify the rebound ratio of the first thermoplastic film 151. As shown by FIG. 8, the intermeshing rollers 122, 124 can be MD intermeshing rollers. In alternative implementations, the intermeshing rollers 212, 214 can be TD intermeshing rollers, DD intermeshing rollers, SELFing rollers, embossing rollers, or other intermeshing rollers. The rollers 212, 214 may be arranged so that their longitudinal axes are perpendicular to the machine direction. Additionally, the rollers 212, 214 may rotate about their longitudinal axes in opposite rotational directions. In various embodiments, motors may be provided that power rotation of the rollers 212, 214 in a controlled manner. As the first thermoplastic film ply 151 passes between the first and second rollers 212, 214, the ridges and/or teeth of the intermeshing rollers 212, 214 can form an incrementally-stretched film 220.

Additionally, the second thermoplastic film 164 can optionally pass between third and fourth intermeshing rollers 216, 218 to incrementally stretch the second thermoplastic film 164. The intermeshing rollers 216, 218 can have a construction similar to that of intermeshing rollers 212, 214, or may differ. As the second thermoplastic film 164 passes between the third and fourth intermeshing rollers 216, 218, the ridges and/or teeth of the intermeshing rollers 216, 218 can form an incrementally-stretched film 222. In alternative implementations, the process 210 may omit incrementally stretching the second thermoplastic film 164. Still further, the process can optionally include continuously stretching, embossing, or otherwise processing the second thermoplastic film 164.

Incrementally stretching one or more of the first and second thermoplastic films 151, 164 can modify and/or increase one or more of the physical properties, increase the surface area, and/or reduce the gauge of one or more of the first and second thermoplastic films 151, 164. Furthermore, incrementally stretching one or more of the first and second thermoplastic films 151, 164 can provide one or more of the first and second thermoplastic films 151, 164 with a visual pattern that can serve to notify a consumer that one or more of the first and second thermoplastic films 151, 164 has been processed to enhance one or more properties.

One will appreciate that when both the first and second thermoplastic films 151, 164 are incrementally stretched, they can undergo the same type and/or degree of stretching. Alternatively, the first and second thermoplastic films 151, 164 can undergo different types and/or degrees of stretching. For example, in one or more implementations, as shown by FIG. 8, the first and second intermeshing rollers 212, 214 and the third and fourth intermeshing rollers 216, 218 can both comprise MD ring rollers, but with different pitches and/or DOEs. By differing the DOEs of the rollers through which the first and second thermoplastic films 151, 164 pass, a manufacturer can alter the rebound ratios of the films. In addition to altering the DOE, a manufacturer can change the speed through which the first and second thermoplastic films 151, 164 respectfully pass through the rollers to modify the degree of stretch and/or the rebound ratio of the films.

Still further, the first and second cylindrical intermeshing rollers 212, 214 can comprise MD ring rollers, while the third and fourth intermeshing rollers 216, 218 comprise TD ring rollers. Alternatively, the first and second cylindrical intermeshing rollers 212, 214 can comprise ring rollers, while third and fourth intermeshing rollers 216, 218 comprise SELFing rollers. Additionally, while not shown in FIG. 8, one or both the first and second thermoplastic films 151, 164 can undergo a second incremental stretching process after respectively passing through the intermeshing rollers 212, 214, 216, 218. For example, one or more of the first and second thermoplastic films 151, 164 can pass through a second, sequential set of intermeshing rollers. For example, the first thermoplastic film 151 can pass through a first set of MD ring rollers and then through a second sequential set of TD intermeshing rollers such that the incrementally-stretched film 220 is both MD and TD ring rolled. Thus, one or more of the first and second thermoplastic films 151, 164 can undergo any number or combination of the incremental stretching processes.

The incrementally-stretched films 220, 222 may then pass between fifth and sixth cylindrical intermeshing rollers 224, 226 to incrementally stretch and lightly laminate the initially separate incrementally-stretched films 220, 222. The intermeshing rollers 224, 226 can have a construction similar to any of the other intermeshing rollers shown or described herein. In at least one implementation, as shown by FIG. 8, the intermeshing rollers 224, 226 comprise TD ring rollers. After passing through the fifth and sixth cylindrical intermeshing rollers 224, 226, tension in the films 220, 222 may be released thereby creating a multi-ply, puckered film 230. The multi-ply, puckered film 230 can then be processed into a bag as explained in relation to FIG. 7. Alternatively, the tension may be released after the film 230 has been processed into a bag.

As alluded to earlier, multi-ply, puckered films and bags including the same of one or more implementations can provide an overall thinner film employing a reduced amount of raw material that nonetheless has maintained or increased loft. The following example presents the results of a series of tests performed on thermoplastic films that were stretched, non-continuously laminated, and released to form multi-ply, puckered films in accordance with one or more implementations of the present invention. This example is illustrative of the invention claimed herein and should not be construed to limit in any way the scope of the invention.

EXAMPLE

A first thermoplastic film of a base film comprising a core ply of Hexene Comonomer, Gas Phase LLDPE with white pigment and outer plies of LLDPE\Slip blend was cold formation MD ring rolled. The MD intermeshing rolls used had a 0.100" pitch and were set at a DOE of 0.100". The first thermoplastic film was MD ring rolled at 180 feet per minute and then wound up on a roll at 300 feet per minute. A second thermoplastic film of the same base film was also cold formation MD ring rolled at various DOEs and various slower speeds than the first thermoplastic film. The difference in speeds is designated as a draw difference percentage. The various speeds and DOEs provided the second thermoplastic film with a different draw ratio than the first thermoplastic film. The various different combinations of DOEs and draw difference percentages are included in Table 1 as samples 1-11. Both the first and second thermoplastic films were then run together through cold formation TD intermeshing rollers to non-continuously laminate the films together. The TD intermeshing rollers had a 0.040" pitch and were set at a DOE of 0.030". The first and second thermoplastic films were cold formation TD ring rolled at 294 feet per minute and then wound at 300 feet per minute. Table I shows comparative properties of the resultant multi-ply, puckered films.

TABLE I

| Sample # | Film 2 MD DOE | Draw Diff. % | % Reduction in Basis Weight | % Change in Loft |
|---|---|---|---|---|
| 1 | 0.100" | 0 | 21.3 | 4.3 |
| 2 | 0.110" | 10 | 29.4 | 33.0 |
| 3 | 0.110" | 5 | 12.5 | 19.1 |
| 4 | 0.110" | 0 | 14.7 | −17.8 |
| 5 | 0.105" | 10 | 13.2 | 30.4 |
| 6 | 0.105" | 5 | 14.0 | 29.6 |
| 7 | 0.105" | 0 | 9.6 | −3.0 |
| 8 | 0.100" | 5 | 5.9 | 32.2 |
| 9 | 0.100" | 0 | 11.8 | 12.2 |
| 10 | 0.105" | 5 | 8.8 | 20.9 |
| 11 | 0.100" | 5 | 1.5 | 39.1 |

As shown by the results of Table I, multi-ply, puckered film of the present invention can provide increased loft. Sample 1, where Film 1 and Film 2 were prepared in the same fashion and had the same rebound ratio, gave a partially discontinuous laminate with only a small 4.3% increase in loft. Table I shows that by stretching Film 1 and Film 2 differently that over 30% increase in loft can be achieved. Furthermore, as shown by samples 2, 3, 5, 6, and 8-11, implementations of the present invention can decrease basis weight (amount of thermoplastic material) while increasing the loft of the film. Additionally, Table 1 shows that the loft of a multi-ply, puckered film can be controlled independent of the basis weight of the film. For example, sample 2 is a multi-ply, puckered film with a low basis weight and a large loft. Sample 6, on the other hand, is a multi-ply, puckered film with a medium basis weight and a large loft. Sample 11 is a multi-ply, puckered film with a high basis weight and a large loft.

Thus, in one or more implementations, a multi-ply, puckered film can include a large increase in loft, more than 1.3 times, while having a small reduction in basis weight, (percent reduction less than 5%). Alternatively, a multi-ply, puckered film can include a large increase in loft, more than 1.2 times, while having a medium reduction in basis weight (i.e., percent reduction between about 10% and 20%). In still further implementations, a multi-ply, puckered film can include a large increase in loft, more than 1.3 times, while having a large reduction in basis weight (i.e., percent reduction between about 20% and 30%).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. A multi-ply, puckered thermoplastic film comprising:
a first ply of a first thermoplastic material having a first ply maximum gauge, wherein the first ply has been cold formation stretched to form comprises alternating thick linear areas of un-stretched material and that alternate with thin linear areas of stretched material;
a second ply of the first thermoplastic material having a second ply maximum gauge and adjacent to the first ply, wherein the second ply is a flat ply;
a plurality of non-continuous bonds securing the thick areas of the first ply directly to the second ply such that the multi-ply, puckered thermoplastic film is devoid of layers between the first ply and the second ply, wherein the bonds between the first ply and the second ply are formed with the first ply in the stretched condition; and
a plurality of puckers in the second thermoplastic ply, the puckers being located between and maintained by adjacent laminated areas and the puckers having a height of at least 1.25 times the sum of the first ply maximum gauge and the second ply maximum gauge;
wherein a loft of the multi-ply, puckered thermoplastic film is increased between 4.3% and 33% while a basis weight of the multi-ply, puckered thermoplastic film has a percent decrease between 10% and 30% compared to a combination of the first and second plies in an un-stretched state.

2. The multi-ply film of claim 1, wherein the puckers have a height of at least 2 times the sum of the first ply maximum gauge and the second ply maximum gauge.

3. The multi-ply film of claim 1, wherein the alternating thick areas and thin areas of the first ply are formed by MD ring rolling.

4. The multi-ply film of claim 1, wherein the alternating thick areas and thin areas of the first ply are formed by both MD ring rolling and TD ring rolling.

5. The multi-ply film of claim 1, wherein the bonds are formed by a cold formation process selected from the group consisting of MD ring rolling, TD ring rolling, strainable network formation, and combinations thereof.

6. The multi-ply film of claim 1, wherein the bonds are formed by a process selected from the group consisting of embossing, adhesive bonding, and combinations thereof.

7. The multi-ply, puckered thermoplastic film as recited in claim 1, wherein the bonds are discontinuous.

8. A multi-ply, cold-formed puckered thermoplastic film comprising:
a first ply of thermoplastic material having a first ply maximum gauge, wherein the first ply has been cold formation stretched by MD ring rolling to form alternating thick layers of un-stretched material and thin areas of stretched material;
a second ply of thermoplastic material having a second ply maximum gauge and adjacent to the first ply;
a plurality of non-continuous, non-heat, pressure bonds securing thick areas of the first ply to the second ply wherein the bonds are formed with the first ply in the stretched condition; and
a plurality of puckers in the second thermoplastic ply, the puckers being located between and maintained by adjacent non-continuous, non-heat, pressure bonds and the puckers having a height of at least 1.25 times the sum of the first ply maximum gauge and the second ply maximum gauge;
wherein a loft of the multi-ply, puckered thermoplastic film has a percent increase between 4.3% and 33% while a basis weight of the multi-ply, puckered thermoplastic film has a percent decrease between 10% and 30% compared to a combination of the first and second plies in an un-stretched state.

9. The multi-ply film of claim 8, wherein the second ply has been stretched prior to lamination and wherein the stretched second ply has a smaller rebound ratio than the first ply.

10. The multi-ply film of claim 8, wherein the second ply is a flat ply.

11. The multi-ply film of claim 8, wherein the non-continuous, non-heat, pressure bonds are formed by a process selected from the group consisting of MD ring rolling, TD ring rolling, strainable network formation, embossing, adhesive bonding, and combinations thereof.

12. A multi-ply, puckered thermoplastic film formed from first and second thermoplastic films, comprising:
a first ply of thermoplastic material having a first rebound ratio, wherein the first ply has been cold formation stretched to form a first plurality of alternating thick areas of un-stretched material and thin areas of stretched material extending in a transverse direction;
a second ply of thermoplastic material having a second rebound ratio differing from the first rebound ratio and adjacent to the first ply, wherein the second ply has been cold formation stretched to form a second plurality of alternating thick areas of un-stretched material and thin areas of stretched material extending in the transverse direction;
a plurality of non-continuous laminated areas bonding some thick areas of the first ply to the second ply wherein the laminated areas are formed with the first ply in the stretched condition the plurality of bonds extending in the machine direction; and
a plurality of puckers in the second thermoplastic film ply, the puckers being located between and maintained by adjacent laminated areas due to relaxation of the first ply, wherein a loft of the puckers is greater than a sum of the first gauge and the second gauge;
wherein a machine direction of the first ply of thermoplastic material is parallel to a machine direction of the second ply of thermoplastic material;
wherein a loft of the multi-ply, puckered thermoplastic film is increased between 4.3% and 33% while a basis weight of the multi-ply, puckered thermoplastic film has a percent decrease between 10% and 30% compared to a combination of the first and second plies in an un-stretched state.

13. The multi-ply, puckered thermoplastic film as recited in claim 12, wherein the thermoplastic material of the first ply is the same as the thermoplastic material of the second ply.

14. The multi-ply, puckered thermoplastic film as recited in claim 12, wherein the first thermoplastic film has been stretched to a greater extent than the second thermoplastic film during formation of laminated areas.

15. The multi-ply, puckered thermoplastic film as recited in claim 12, wherein the first thermoplastic film and the second thermoplastic film have been MD ring rolled.

16. The multi-ply, puckered thermoplastic film as recited in claim 12, wherein the laminated areas are formed by TD ring rolling.

17. The multi-ply, puckered thermoplastic film as recited in claim 12, wherein the laminated areas are formed by SELFing.

18. The multi-ply, puckered thermoplastic film as recited in claim 12, wherein the laminated areas are formed by embossing.

* * * * *